US006852341B2

(12) United States Patent
Rodriguez-Kabana

(10) Patent No.: US 6,852,341 B2
(45) Date of Patent: Feb. 8, 2005

(54) AZIDE METHOD AND COMPOSITION FOR CONTROLLING DELETERIOUS ORGANISMS AND FOR STIMULATING BENEFICIAL ORGANISMS

(75) Inventor: Rodrigo Rodriguez-Kabana, Auburn, AL (US)

(73) Assignee: Auburn University, Auburn, AL (US)

( * ) Notice: Subject to any disclaimer, the term of this patent is extended or adjusted under 35 U.S.C. 154(b) by 140 days.

(21) Appl. No.: 10/268,049

(22) Filed: Oct. 8, 2002

(65) Prior Publication Data
US 2003/0082241 A1 May 1, 2003

Related U.S. Application Data

(63) Continuation-in-part of application No. 09/974,288, filed on Oct. 9, 2001.
(60) Provisional application No. 60/238,943, filed on Oct. 10, 2000.

(51) Int. Cl.[7] .................. A01N 59/00; A01N 37/18; A01N 33/02; A01N 33/26; A01N 63/02
(52) U.S. Cl. .................. 424/719; 424/600; 424/682; 424/722; 424/725; 514/2; 514/8; 514/12; 514/13; 514/18; 514/21; 514/151; 514/400; 514/419; 514/423; 514/556; 514/561; 514/562; 514/563; 514/564; 514/565; 514/567; 514/579; 514/649; 514/663; 514/664; 514/667; 514/669; 514/671; 514/970; 514/973; 504/188; 504/362; 504/364
(58) Field of Search .................. 514/2, 8, 12, 13, 514/18, 21, 151, 400, 419, 423, 556, 561–565, 567, 579, 649, 663, 664, 667, 669, 671, 970, 973; 504/188, 362, 364; 424/600, 682, 719, 722, 725

(56) References Cited

U.S. PATENT DOCUMENTS

| 1,819,399 A | | 8/1931 | Wesenberg ................. 423/409 |
| 3,376,126 A | | 4/1968 | McConnell et al. ......... 504/163 |
| 3,376,127 A | | 4/1968 | McConnell et al. ......... 504/151 |
| 3,583,987 A | | 6/1971 | Berrer et al. ............ 260/249.6 |
| 3,771,994 A | | 11/1973 | McConnell et al. ......... 504/113 |
| 3,812,254 A | | 5/1974 | McConnell ................. 514/160 |
| 3,880,646 A | | 4/1975 | McConnell et al. ......... 504/113 |
| 4,132,780 A | | 1/1979 | McConnell ................. 424/600 |
| 4,555,262 A | * | 11/1985 | Thummel et al. ........... 504/214 |
| 5,185,264 A | * | 2/1993 | Makela ...................... 436/18 |

FOREIGN PATENT DOCUMENTS

| EP | 0 102 924 A2 | 8/1983 |
| JP | 09-227315 | 2/1997 |

(List continued on next page.)

OTHER PUBLICATIONS

Derwent abstrct 1996–184644, abstracting JP 8–59416 (1996).*

(List continued on next page.)

*Primary Examiner*—John Pak
(74) *Attorney, Agent, or Firm*—Knobbe Martens Olson & Bear LLP

(57) ABSTRACT

Disclosed is both a method and composition for controlling deleterious organisms, such as insects, nematodes and weeds while maintaining beneficial soil organisms, by applying a compound comprised of a liquid medium and comprising an azide and an amino acid polymer. The azide can be selected from the group consisting of sodium azide and potassium azide or a combination of the two. The composition provides an effective pesticide, without causing significant harm to the environment. The composition may be applied to soil to control a population of a deleterious organism.

35 Claims, 14 Drawing Sheets

FOREIGN PATENT DOCUMENTS

| JP | 09-095402 | 8/1997 |
| JP | 10-146150 | 2/1998 |
| JP | 10-117662 | 12/1998 |
| JP | 11-209210 | 3/1999 |
| JP | 11-199416 | 7/1999 |

OTHER PUBLICATIONS

Office Action for co–pending U.S. Appl. No. 10/268,050, mailed May 5, 2004.
Office Action for co–pending U.S. Appl. No. 09/974,288, mailed Mar. 26, 2003.
Office Action for co–pending U.S. Appl. No. 09/974,288, mailed Feb. 10, 2004.
Advisory Action for co–pending U.S. Appl. No. 09/974,288, mailed May 20, 2004.
Patent Abstracts of Japan, Publication No. 09–5402 "Method for Preventing Crop Injury of Azide Compound and Preventing Agent Therefor" Apr. 8, 1997; abstract and computer translation.
Patent Abstracts of Japan, Publication No. 09–227315 "Growth of Useful Plant and Soil Treating Agent for Controlling Damage by Soil Propagating Virus" Sep. 2, 1997; abstract and computer translation.
Patent Abstracts of Japan, Publication No. 10–117662 "Treatment of Soil to Remove Pest of Soil" May 12, 1998; abstract and computer translation.
Patent Abstracts of Japan, Publication No. 10–146150 "Growth of Useful Plant and Soil Treating Agent for Controlling Soil Insect Pest" Jun. 2, 1998; abstract and computer translation.
Patent Abstracts of Japan, Publication No. 11–199416 "Granular Soil Treatment Agent for Controlling Organism" Jul. 27, 1999; abstract and computer translation.
Patent Abstracts of Japan, Publication No. 11–209210 "Prevention of Chemical Injury by Azide Compound" Aug. 3, 1999; abstract and computer translation.
Chalfant, R. B., et al., "Reflective Film Mulches, Millet Barriers, and Pesticides: Effects on Watermelon Mosaic Virus, Insects, Nematodes, Soil–borne Fungi, and Yield of Yellow Summer Squash," *J. Amer. Soc, Hort Sci.*, 102(1) : 11–20 (1977).
Hughes, T. D., and Welch, L.F., "Potassium Azide as a Nitrification Inhibitor," *Agronomy Journal*, vol. 62:595–599, (Sep.–Oct. 1970).
Bradbury, F. R., et al., "The Nematicidal Properties of Azides," *Ann. Appl. Biol.* 45(2) :241–250 (1957).
Accession No. JP09269326, "Stable liquid immuno–agglutination reagent," Oct. 14, 1997 (Abstract).
Chalfant, et al., "Reflective Film Mulches, Millet Barriers, and Pesticides: Effect on Watermelon Mosaic Virus, Insects, Nematodes, Soil–borne Fungi, and Yield of Yellow Summer Squash," *J. Amer. Soc. Hort. Sci.*, 102(1):11–15 (1977).
Hughes & Welch, Potassium Azide as a Nitrification Inhibitor, *Agronomy Journal*, vol. 62:595–599, (Sep.–Oct. 1970).
Bradbury, et al., "The nematicidal Properties of Azides," *Ann. Appl. Biol.* 45(2):241–250 (1957).
JP 09269326, "Stable liquid immuno–agglutination reagant," Oct. 14, 1997 (Abstract).
EPO Search Report for corresponding application EP 019776772.

* cited by examiner

AZIDE METHOD AND COMPOSITION FOR CONTROLLING DELETERIOUS ORGANISMS AND FOR STIMULATING BENEFICIAL ORGANISMS

RELATED APPLICATIONS

This application is a continuation-in-part of application Ser. No. 09/974,288, filed on Oct. 9, 2001, which claims the benefit of provisional Application No. 60/238,943, filed on Oct. 10, 2000, the entire teachings of both of which are incorporated herein by reference.

BACKGROUND OF THE INVENTION

The present invention relates generally to the fields of biology and agriculture and more particularly to compositions and methods for use as pesticides and herbicides.

The control of insects, plant pathogens, nematodes and weeds is of central importance to the agriculture industry. In particular, the substantial reduction or elimination of nematode populations in soils is critical to initial plant growth, productivity and life-span. Pathogenic fungi and nematodes develop on the extensive root systems of both annual and perennial crops, damaging them severely. Moreover, they persist in the soil after crop removal and need to be eliminated before replanting of new crops.

Approaches which have been used successfully to combat plant pathogens and nematodes have been crop rotation, following for at least four years, use of pathogen and nematode-resistant crops and soil fumigation. Resistance to plant pathogens and nematodes is available only in a few crops, and resistant cultivars may not be developed in the foreseeable future for many crops of significant commercial interest. Therefore, soil fumigation remains the best alternative for control of plant pathogens and nematodes.

Methyl bromide ($CH_3Br$) is the most widely used and most universal fumigant in the world. It is used extensively for soil fumigation, as a commodity quarantine treatment (export and imports) to control a variety of pests on numerous crops, and as a structural fumigant for wood destroying pests.

Methyl bromide (hereinafter referred to as "MBr") is categorized as an ozone depleting chemical with an ozone depleting potential (ODP) of greater than 0.2 compared to trichlorofluoromethane (cfc 11), a refrigerant used as a reference gas having an ODP of 1.

Evidence on the loss of MBr to the atmosphere after soil fumigation indicates that of the total amount applied to the soil for fumigation, approximately 87% is lost to the atmosphere within seven days. On reaching the stratosphere MBr undergoes photo-oxidation, releasing bromine atoms which enter the ozone depletion cycle. MBr loss from fumigated soils is further supported by studies which indicated a loss of as much as 70% of the applied MBr to the atmosphere through the tarp and after the tarp is removed.

As currently available alternatives to MBr are less effective and/or more expensive, the removal of MBr will be very costly. Annual losses to U.S. producers and consumers is estimated to be in the region of 1.5 billion dollars. This figure does not account for the losses due to post harvest, quarantine and structural fumigation losses. MBr removal would most adversely affect such commodities as tomatoes, strawberries, peppers, melons and ornamentals. The loss of MBr would thus be extremely costly to both agricultural producers and consumers as well as having a substantial impact on the U.S. economy. Nonetheless, it is the general consensus of those working in the field that no approach is currently available that will achieve the same level of broad-spectrum pest management as MBr; chemical and non-chemical approaches that are available can provide some level of agricultural pest management, but generally with narrower activity and lower crop yields and quality. Therefore, there is clearly a need for alternatives to Mbr.

Various azide formulations have also been considered for controlling populations of deleterious organisms. For example, sodium or potassium azide can dissociate to form hydrazoic acid, which can destroy or inhibit many deleterious organisms. However, it has been difficult to appropriately formulate an azide composition which effectively provides an appropriate balance of controlling deleterious organisms, while not impairing beneficial organisms.

SUMMARY OF THE INVENTION

The present invention provides both compositions and methods for controlling a population of deleterious organisms in soil without causing significant harm to environment. The deleterious organisms that are the target of this invention include any pests, such as, for example, insects, fungi, nematodes, weeds and any other organism that may adversely affect agricultural endeavors. Such deleterious organisms may be controlled by applying an effective amount of an azide to a soil. A dispersal medium containing an azide can be applied to an environmental system to control a population of deleterious organisms. For example, an aqueous solution containing an azide may be applied to soil, whereby a population of target pest organisms within the soil is controlled. Application of the liquid may include applying to a soil an amount of azide effective in controlling the population of one or more targeted pests. The azide contained within the liquid may be in the form of ionic azide ($N_3^-$) and may be derived from any appropriate azide compound. For example, the azide may be sodium azide, potassium azide or a combination of both sodium and potassium azide.

The azide compositions of this invention contain polymers of three or more amino acids in a serial array, linked through peptide bonds, which may be in the form of an "oligopetide", an "polypeptide" or a "protein". The term "polypeptide" includes proteins, protein fragments, protein analogues, oligopeptides and the like. The term "polypeptides" further contemplates polypeptides as defined above that include chemically modified amino acids or amino acids covalently or noncovalently linked to labeling ligands. Most preferred are amino acid polymers which contain phosphorous, calcium, magnesium, potassium and other plant nutrients.

The azide composition can further include one or more additives such as detergents, pH buffering agents, colorants and amines. A detergent may also function as a wetting agent thereby improving the delivery of the liquid composition of the present invention to the soil.

The azide compositions can further contain additives to maintain the pH of the liquid medium above about 7.0. The alkalinity can be achieved by an organic or inorganic pH buffering agent, the addition of hydroxyl ions or a combination thereof.

The composition of the present invention can serve generally as a pesticide. The composition can be used more specifically as a herbicide, an insecticide, a fungicide and/or a nematocide or a combination thereof, depending upon the needs of the user to control these deleterious organisms.

A given soil also contains numerous beneficial organisms. For example, microbivorous nematodes (also know as

*saprophagous*) beneficially are involved in organic matter transformations in soil, resulting in improvements and long-term maintenance of soil fertility and soil health. The azide formulations of the present invention eliminate or control deleterious organisms, but do not unduly negatively impact beneficial organisms, due to the selectivity of the azide, its concentration and/or its method of application and the presence of amino acid polymers (e.g., protein) which foster growth of beneficial organisms.

The present invention also encompasses a kit for preparing a pesticidal composition, comprising azide and amino acid polymer and instructions for preparing the pesticidal composition and applying the pesticidal composition to an environmental system, such as, for example, soil, to control a population of a targeted deleterious organism therein. The kit can further comprise one or more additives such as, but not limited to, a detergent, an amine, and a pH buffering agent or any combination thereof.

The invention also encompasses azide-containing solutions that may be diluted in a liquid medium and applied to an environmental system, such as, for example, soil, in order to control deleterious organisms contained therein.

The invention further provides agricultural systems comprising an azide for controlling a population of deleterious organisms and one or more other components such as, for example, a fertilizer to promote crop growth.

Additional objects and aspects of the present invention will become more apparent upon review of the detailed description set forth below when taken in conjunction with the accompanying figures, which are briefly described as follows.

DETAILED DESCRIPTION OF THE INVENTION

Figure 1:
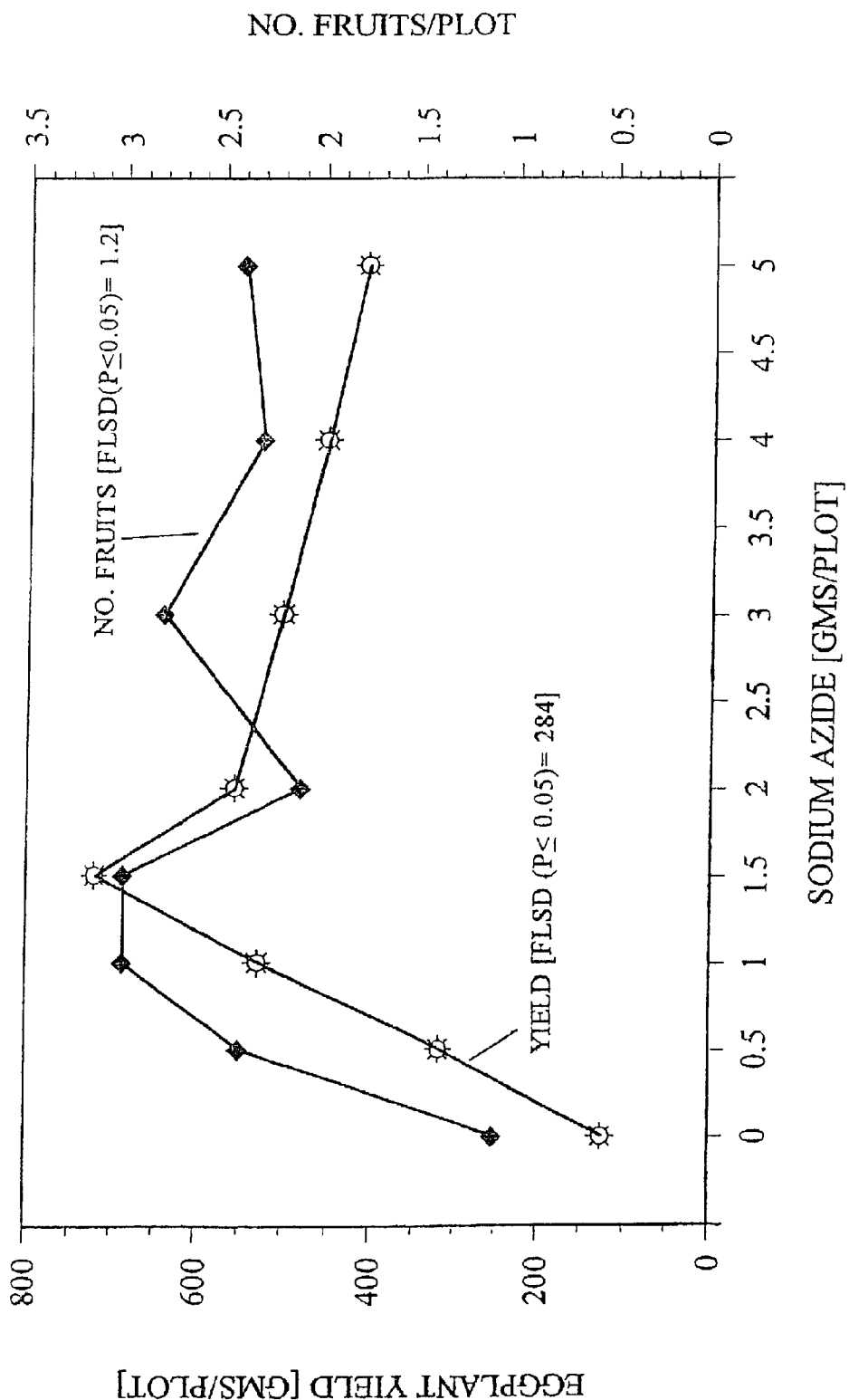
FIG. 1 is a graph illustrating the fruit yield of eggplants grown in soil treated with increasing doses of an aqueous solution of sodium azide.
Figure 2:
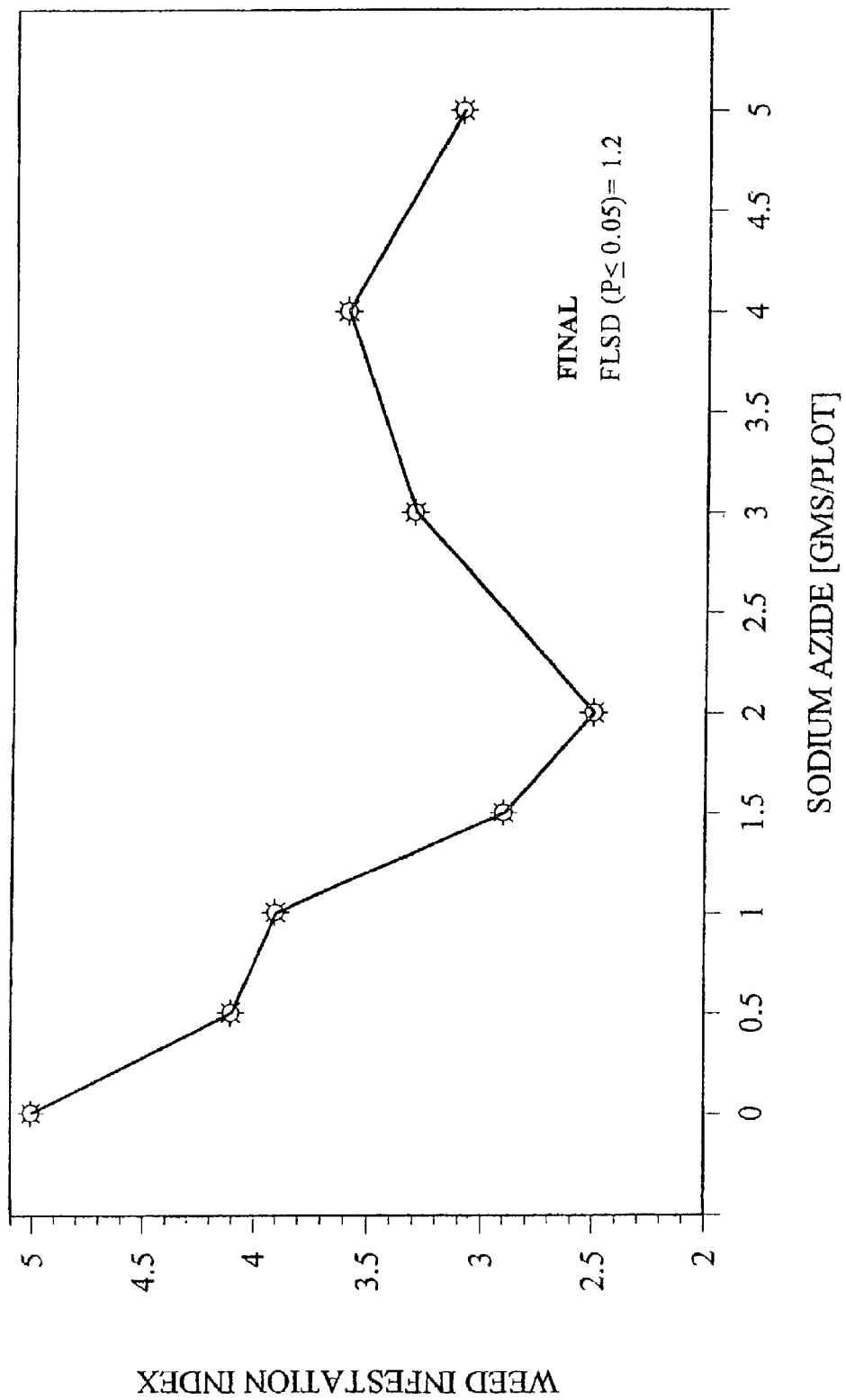
FIG. 2 is a graph illustrating the weed count or infestation in soil treated with increasing doses of an aqueous solution of sodium azide.
Figure 3:
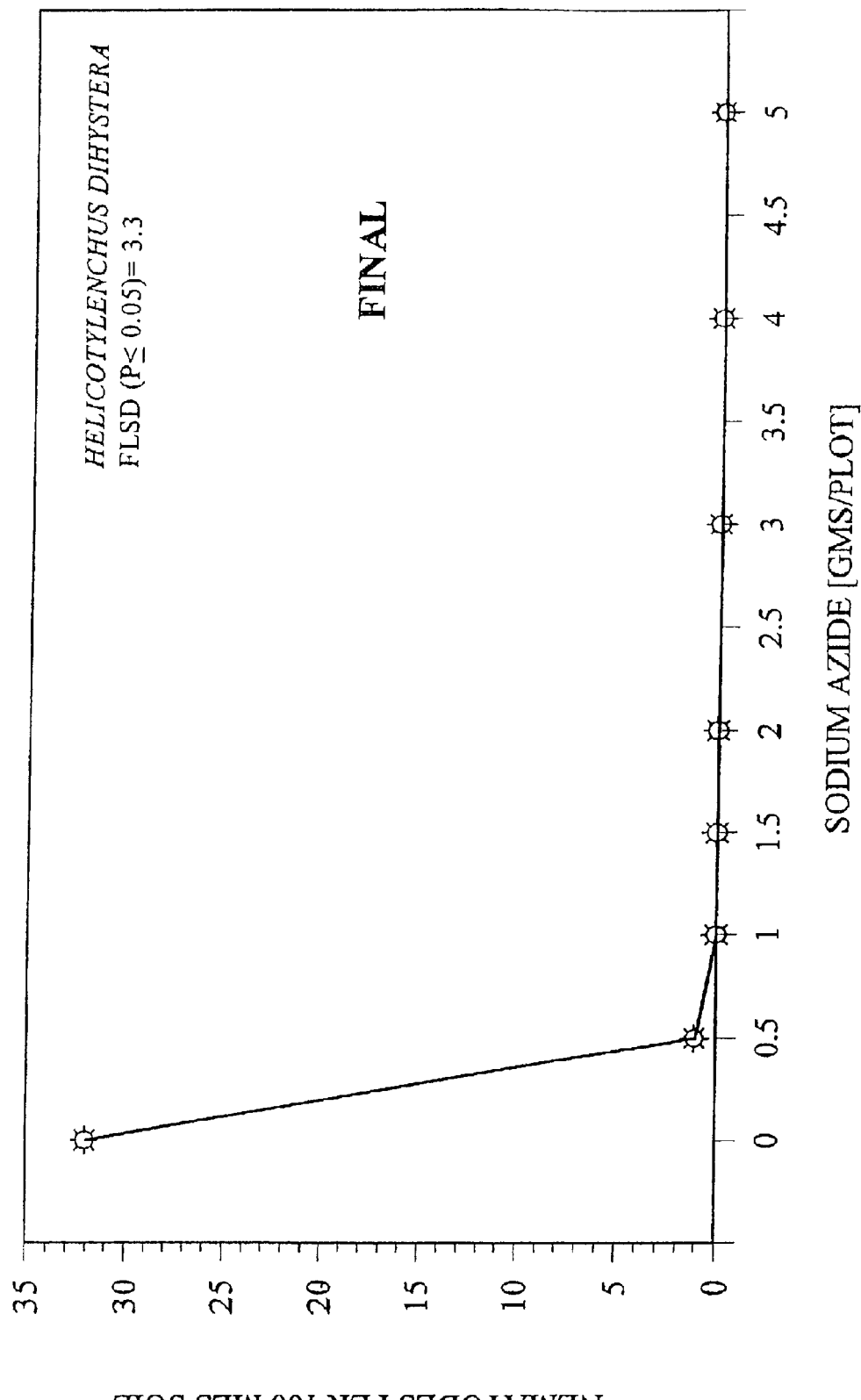
FIG. 3 is a graph illustrating the count of the nematode *Helicotylanchus dihystera* in soil treated with increasing doses of an aqueous solution of sodium azide.
Figure 4:
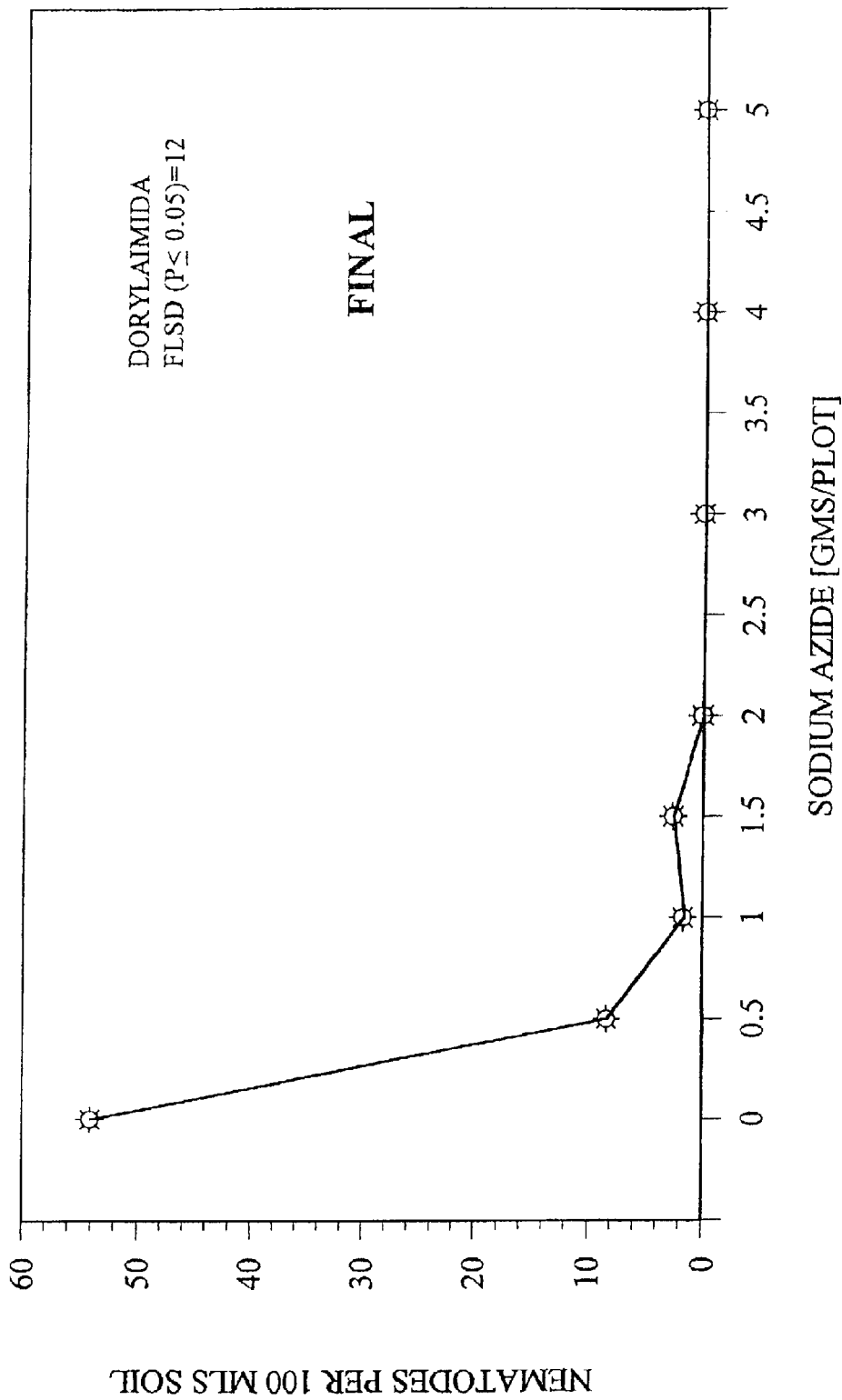
FIG. 4 is a graph illustrating the count of the nematode *Dorylaimida* in soil treated with increasing doses of an aqueous solution of sodium azide.

The present invention provides methods and compositions for controlling a population of a deleterious organism such as, but not limited to, an insect, a nematode or a weed or a combination thereof, by applying a composition comprised of a liquid medium, azide and amino acid polymer. The liquid medium is both safe and stable for use in irrigation systems, such as in a drip irrigation line and may be used in formulations with plant nutrients and other pest control agents. The azide can be an ionic azide. Exemplary ionic azides include, but are not limited to, sodium and potassium salts or any combination thereof. The azide may be produced through the introduction of an azide salt to an aqueous medium. While sodium and potassium azides may be used most commonly, any azide salt, such as, for example, ammonium, calcium, zinc azides, are also appropriate. The compositions of the present invention provide effective nematocides having herbicidal properties, and do not cause significant or permanent harm to the environment.

Prior to application to the soil, care in handling is required to help assure that the azide component does not dissociate to form hydrazoic acid and in the case of sodium azide, to ionic sodium and nitrogen. Such dissociation can also prematurely occur after application to lower pH soils (e.g., <6–7) and in such applications, the presence of amines or pH buffering agents can help minimize or control the dissociation.

The term "controlling" as used herein refers to regulating a population of a deleterious organism that may be harmful to an agricultural product. The population may be regulated by the compositions and methods of the present invention so that the organism is killed, thereby reducing the viable populations such as by nematocidal, fungicidal, herbicidal or insecticidal activity or the like. The methods and compositions of the present invention may maintain and not allow a population of a deleterious organism to increase or may prevent an invasion of a soil by a deleterious organism.

The term "azide" as used herein refers to any compound having the $N_3^-$ moiety therein. The azide can be a metal azide wherein the metal is an alkali metal such as potassium, sodium, lithium, rubidium or cesium. The metal can be a transition metal such as, but not limited to, iron, cobalt, nickel, copper or zinc. It is understood that certain metallic azides may be formed in solution by mixing sodium azide or the like with a metallic salt such as, for example, copper sulfate. The azide of the present invention can also be an organic azide or ammonium azide. Some metal azides such as $Cu(N_3)_2$ and $Pb(N_3)_2$, are explosive and if such azides are used, precautions should be taken (e.g., copper-containing fittings, such as brass or bronze, should not be used).

Azide formulations of the present invention containing both the amino acid polymer and an amine are particularly effective, in that the amino acid polymer facilitates the formation and release of microbial deaminases in soil which remove $NH_2$-groups from the amine, thereby forming $NH_4^+$—N. Since sodium and potassium azides are strong inhibitors of soil nitrification, the resulting ammoniacal N is retained in soil and used by plants rather than be leached out into the environment as nitrate.

The azide compositions of the present invention provide an amount of azide in the soil, which is effective for controlling a population of a deleterious organism therein. Preferably, the azide compositions contain up to about 40% (preferably about 10 to 20%) of azide (preferably sodium azide) and up to about 20% (preferably of about 5 to 15%) of the amino acid polymer in an aqueous dispersal medium, said percentages being based upon the weight of said dispersal medium. Most preferably, the specified amino acid polymers would be present as about 5 to 10% of casein and the composition would further contain up to about 5% of detergent (most preferably about 0.01 to 0.5% of sodium lauryl sulfate).

The amino acid polymer of the present invention include oligopeptides, polypeptides and proteins. For example, the protein casein is preferred. Casein is soluble in dilute alkalis and other materials, such as ethanolamine and, when added to soils, stimulates the activities of proteolytic microorganisms. Casein is available from both animal and vegetable (e.g., soybean meal) sources. It is a mixture of phosphoproteins, amphoteric forming water soluble salts with Na, K, Ca, etc. Casein is rich in tyrosine and tryptophan. When properly compounded and added to soil, casein will optimally stimulate proteolytic activities in soil which are inimical to nematodes and other soil borne pests, and at the same time, deliver a healthy dose of basic plant nutrients. The increased microbial proteolytic activity may further be antagonistic to plant parasitic nematodes and other soil borne pests.

Suitable amino acid polymers for use in the compositions of the present invention include, but are not limited to, proteins derived from a cereal meal such as soybean meal, wheat glutten, cottonseed meal, maize meal, peanut meal, or wheat meal. Other suitable proteins can include zein, gluten, gelatin and the like or protein obtained from animal sources such as whey. Collagen and gelatin are less useful in that they are simple proteins which contain virtually no tyrosine, tryptophan or phenyl alanine, which are present in other of the listed amino acid polymers and do stimulate phenol oxidase activity in soil (i.e., humus formation) to a significant degree.

The term "liquid medium" as used herein refers to an aqueous or organic fluid at least partially in the liquid phase under ambient conditions. Suitable fluids include, but are not limited to, water, an oil, an emulsion, a liquid organic compound such as, for example, ethanolamine, ethanol and the like.

The term "amine" as used herein means an amine selected from group consisting ethanolamine, butylamine, diethylamine, dimethylamine, phenylethylamine, alkonoamines (such as monoethanolamine, diethanolamine and diethylethanolamine), phenylethylamine, and mixtures thereof. The amine components of the compositions of the present invention can also provide an additional source of nitrogen for a crop planted in the soil. The amines should be selected for compatability with a given application (e.g., melamine has limited solubility in water and is phytotoxic to a number of species).

Ethanolamine is most preferred in that it optimally enhances the azide's functionality by helping to prevent the azide from dissociating and forming hydrazoic acid prematurely. Prior to application (e.g., during manufacture, handling, and other points prior to application), it is important that the azide be stabilized against such dissociation. Ethanolamine stabilization provides this pre-application stabilization, and importantly, does not impair the azide's efficacy when applied to the soil.

Further, ethanolamine desirably facilitates a measured diffusion of the azide in the soil from its point of application before the azide dissociates and releases hydrazoic acid. Additionally, ethanolamine is readily biodegradable, which is an important attribute for any pesticide formulation ingredient.

The term "chelating agent" as used herein refers to any organic or inorganic compound that will bind to a metal ion having a valence greater than one, and includes, but is not limited to, organic chelating agents such as ethylenediamenetetracetic acid (EDTA), triethylene tetramine dihydrochloride (TRIEN), ethylene glycol-bis (beta-aminoethyl ether)-N,N,N', N'-tetracetic acid (EGTA), diethylenetriaminpentaacetic acid (DPTA), and triethylenetetramine hexaacetic acid (TTG), deferoxamine, Dimercaprol, Edetate calcium disodium, zinc citrate, penicilamine succimer, Editronate or any other chelating agent, salt or combination thereof, known to one of ordinary skill in the art, and which will chelate divalent metal ions such as, but not only $Ca^{2+}$, $Mg^{2+}$, $Mn^{2+}$, $Fe^{2+}$, and $Zn^{2+}$.

The term "pH buffering agent" as used herein refers to any organic or inorganic compound or combination of compounds that will maintain the pH of a solution to within about 0.5 pH units of a selected pH value. A "pH buffering agent" may be selected from, but is not limited to, Tris (hydroxymethyl) aminomethane (tromethaprim; TRIZMA base), or salts thereof, phosphates, amino acids, polypeptides or any other pH buffering agent or combination thereof.

The term "detergent" and "surfactant" as used herein refer to an amphipathic compound, either neutral or ionic in nature, which is soluble in water, such as sodium lauryl sulfate, which is preferred.

Sodium and potassium azides are typically first formulated as granules (attapulgite clay, diatomaceous earth) or they can be formed in a variety of liquid formulations. The stability of azide formulations is enhanced at pH levels of greater than about 8.7. For the control of pests such as nematodes and fungi such as *Armillaria, Verticillium*, and the protection of deep-rooted crops such as grapes, fruit, and nut trees, liquid formulations are preferred.

The delivery of an azide to a desired application zone may be difficult if the reactivity of the azide in the soil-air space and atmosphere is too rapid and results in an effective concentration of the active compound that is too low for pest control. The specified amines aids in increasing the effectiveness of the liquid medium in such conditions. Thus, the liquid medium can be modified depending upon the soil conditions in which the composition of the present invention is used such as, for example, by increasing the pH of the liquid medium for application to an acidic soil.

Aqueous azide solutions can be further enhanced in an alkaline solution by the addition of pH buffering agents such as, hydroxyl ions such as in the form of sodium or potassium hydroxide or the like, or by adding carbonates and phosphates. Some pH buffering agents may not be desired, however, when used with irrigation waters having, for example, a high calcium ion content. Calcium may combine with solubilized carbonates and/or phosphates of the compositions of the present invention to form calcium carbonate or phosphate precipitates that may corrode or clog irrigation systems. If precipitation is not a concern, any appropriate pH buffering agent may be used, such as, for example, ammonium, sodium or potassium phosphates, ammonium, sodium or potassium carbonates, ammonium, sodium or potassium citrates, acid-salt systems with pH buffering capacity, organic buffers such as Tris and the like, or hydroxyl ions that will maintain, either singly or in combination, a pH in the liquid medium of greater than about 8.7.

Suitable detergent or surfactants can be added such as, but not limited to, sodium lauryl sulfate; Tween 20 [polyoxyethylene (20) sorbitan monolaurate]; Tween 40 [polyoxyethylene (20) sorbitan monopalmitate; Tween 40 [polyoxyethylene (20) sorbitan monopalmitate; Tween 60 [polyoxyethylene (20) sorbitanmonostearate; Tween 80 [polyoxyethylene (20) sorbitan monostearatepalmitate; Tween 85 [polyoxyethylene (20) sorbitan trioleate]; soaps, (i.e. salts of Na, K or ammonium and various fatty acids [ammonium oleate, potassium stearate, etc.]); and tergitol. By using a detergent, the liquid medium can be stabilized without the problem of forming calcium precipitates. The detergent may further cleanse an irrigation system that is used to apply a composition of the present invention to a soil. It is further contemplated to be within the scope of the present invention for the detergent to have wetting properties that may increase the dispersal of the composition of the present invention in the soil.

The azide formulations of this invention are preferably applied to the soil by drip irrigation. In other preferred embodiments, spray or other forms of soil application with subsequent soil tilling (i.e., after the azide is applied) is most desirable. Other conventional or suitable means of application can also be employed. The method of application is preferably selected to disperse a given azide formulation of this invention in the area containing the targeted deleterious organisms. Some pesticidal compositions, such as methyl bromide, are applied as gaseous phase fumigant that is injected into the soil in areas in which the crops are to be planted, but disperses broadly into the surrounding soil. The formulations of this invention are preferably applied as liquid formulations, by drip irrigation or spray application/rototill methods in pre-planting operations to utilize the selectivity of the azide formulation to particular deleterious organisms and to maximize the azide's contact with the soil regions in which these deleterious organisms are prevalent. In this manner, the extent of application can be more precisely controlled. For example, for a given soil type (e.g., sandy or clay type) the depth of penetration of a given quantity of applied aqueous formulation to the soil can be estimated or determined empirically and controlled to a significant degree. This is particularly advantageous in the practice of this invention, in that azide formulation can be applied to the upper zones of the crop area to eliminate or reduce the presence of weeds (e.g., nutsedge which has a root depth of 3–6 inch), without eliminating beneficial microorganisms which exist in deeper soil zones. Although the invention is not limited to the mechanism by which the azide functions, it is believed the azide can be absorbed into the root structure and the azide will then dissociate to form hydrazoic acid in the root.

Additionally, control of the depth of application allows the azide to remain present in the zones those to which it was applied and allows for the reduction or elimination of azide from those zones by subsequent application of additional water (e.g., one of more subsequent drip or spray applications) to transport residual azide (e.g., azide not taken up by the weeds in the application zone) to lower depths in the soil. The remaining, lower concentrations of azide would be available and would control deleterious organisms in these lower regions, for which a lower concentration of azide would be sufficient, or indeed desirable, so as not to unduly impair beneficial organisms. As an example, in a pre-planting mode, the azide formulation can be applied to a depth of about 18 inches (e.g., the root depth of tomato plants) to control deleterious organisms that would otherwise interfere with tomato production, allowing uptake of azide by a deleterious plant's root system. The subsequent application of additional water would eliminate or minimize residual azide in this region of the soil, reducing the impact on the tomato plants.

The present invention is further illustrated by the following examples, which are provided by way of illustration and should not be construed as limiting.

EXAMPLE 1

Control of Nematodes and Weeds

In this example, the efficacy of pre-plant applications of $NaN_3$ for control of plant parasitic nematodes and weeds was studied in a microplot experiment using the aqueous formulation of the chemical. The formulation contained 5% sodium azide dissolved in demineralized water containing 0.5% sodium lauryl sulfate; final pH of the solution was 9.8. The square microplots of 1 ft$^2$ [929 cm$^2$] and 2 feet [61 cms] deep having an open-bottom were used. Each microplot was delimited by a terra-cotta chimney flue. The soil filling the plot was a sandy loam [pH=6.2; organic matter content <1.0%; C.E.C <10 meq/100 g soil] and was infested with the nematodes: *Meloidogyne incognita* [root-knot], *Paratrichodorus minor* [stubby root], *Tylenchorhynchus claytoni* [stunt], and *Helicotylenchus dihystera* [spiral]. Weeds introduced into the plots were principally crabgrass [*Digitaria sanguinalis*], yellow nutsedge [*Cyperus esculentum*], pigweed [*Amaranthus* spp.], and morning glories [*Ipomea* spp., *Jacquemontia tamnifolia*].

Applied to the plots was the aqueous formulation of $NaN_3$ diluted in irrigation water and delivered by drenching [2 L/plot] at amounts of: 0, 0.5, 1.0, 1.5, 2.0, 3.0, 4.0, and 5.0 g sodium azide/plot. The plots were covered with standard polyethylene [1 mil] and after 10 days the cover was removed, the number of weeds was determined, soil samples for nematological analyses were taken and each plot was planted with two 3-week old 'Black Beauty' eggplant [*Solanum melongena*] seedlings. The plants were grown for 2 months and data were collected on yield, weed infestation and nematode populations. There were no nematodes in the planting time samples from plots treated with the solution of $NaN_3$ In contrast, soil from control plots were infested with all nematode species. When planted, there were no weeds in plots treated with all but the two lowest rates of $NaN_3$. Yield and number of fruits increased directly in response to $NaN_3$ rates from 0–1.5 g/plot and leveled out with no additional increases obtained in response to higher rates. At the end of the experiment there were no plant parasitic nematodes and no significant weed infestation in plots with the three highest rates of the chemical but there were significant populations of the parasites and weeds in plots treated with ≦2.0 g $NaN_3$ rates. The results of Example 1 are illustrated in FIGS. 1–4.

EXAMPLE 2

Control of Root Knot

In this example, the value of $NaN_3$ solution for the suppression of the cotton wilt complex [*Fusarium*

*oxysporum* f sp. *vasinfectum×Meloidogyne incognita*] was investigated in a greenhouse experiment with soil from a field having a severe wilt problem. The soil was apportioned in one kg amounts in 4 L plastic bags and was treated with an aqueous formulation of $NaN_3$ to have rates of: 10, 20, 30, 40, 50, 60, 70, 80, 90, and 100 mgs a.i./kg soil. The aqueous formulation was a solution containing 1% [w/v] $NaN_3$ in water containing 0.5% sodium lauryl sulfate with pH=9.8. After thorough mixing, the contents of a bag were poured into 1 L capacity, 10-cm-diam cylindrical plastic pots which were then covered with standard polyethylene [1 ml]. Each rate and the no treatment control was represented by 7 replications [pots] arranged in a randomized complete block design. Ten days after application of the chemical solution, the pots were uncovered and 5 seed of "Rowden" cotton [*Gossypium hirsutum*] were planted in each pot. The resulting plants were grown for 8 weeks. When the plants were removed after 8 weeks, soil samples were collected for nematological analyses. The shoots and roots of the plants were weighed and the root systems were examined and indexed for disease severity symptoms. Following examination, the roots were incubated to determine nematode populations.

Figure 5:
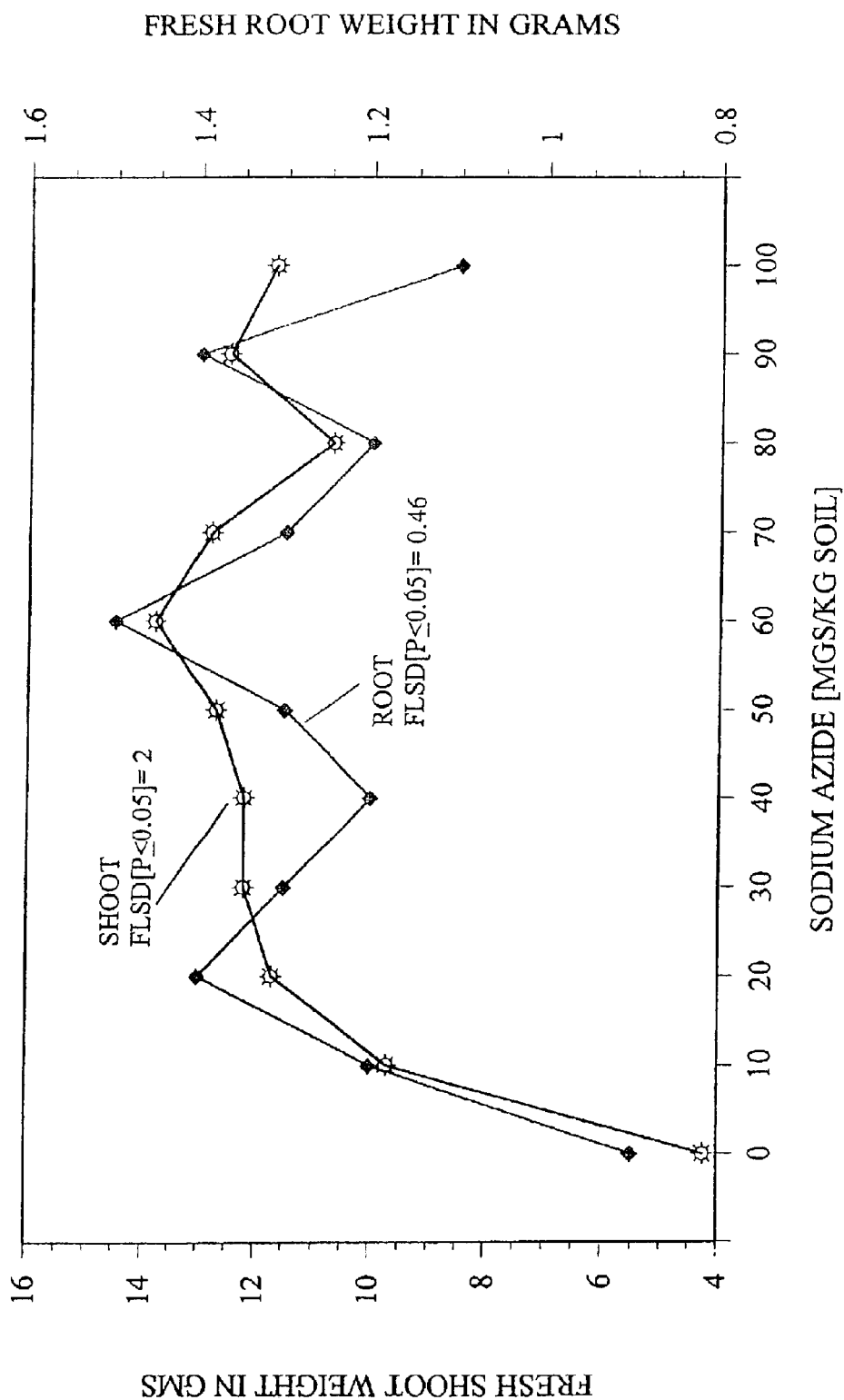
FIG. 5 illustrates a graph comparing both the fresh shoot weight and fresh root weight of cotton grown in soil treated with increasing doses of an aqueous solution of sodium azide.
Figure 6:
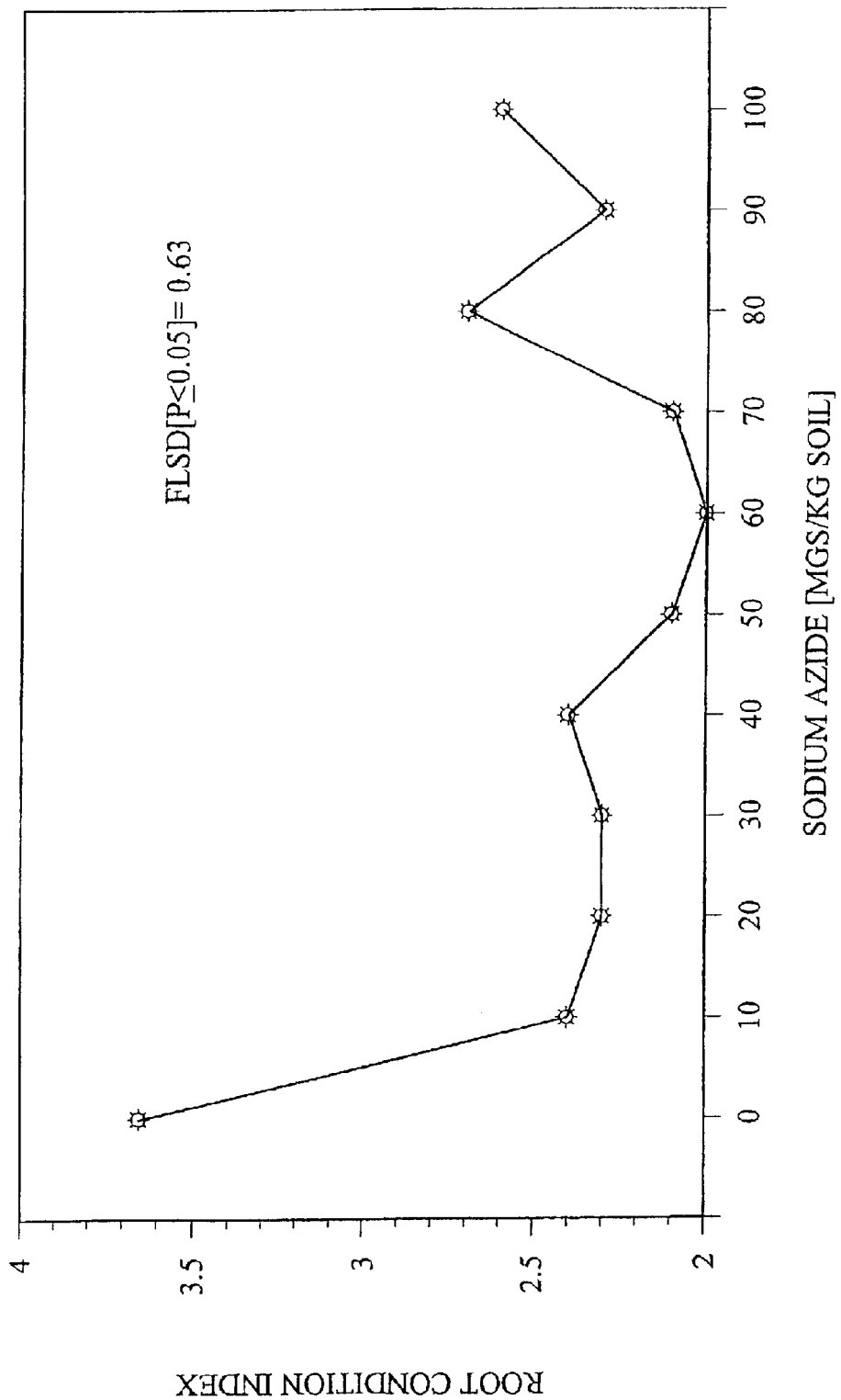
FIG. 6 is a graph illustrating the root condition index of cotton count of cotton grown in soil treated with increasing doses of an aqueous solution of sodium azide.

The results of the analysis indicated that at all $NaN_3$ dosages the plant parasitic nematodes were eliminated from the soil and roots. Sharp increases in weights of shoots and roots were recorded in response to $NaN_3$ application rates in the range 10–60 mgs/kg soil with no additional weight increments being obtained with rates $\geq 70$ mgs/kg soil. Cotton root health [root condition index] was markedly improved in response to all $NaN_3$ dosages, root systems of plants from pots with the 10 mg-rate were as healthy looking as those from pots treated with all other dosages of the compound. Results indicate that $NaN_3$ may be useful for suppression of Fusarium wilt complex and that rates required for wilt control are below those needed for broad-spectrum herbicidal activity. The results of Example 2 are further illustrated in FIGS. 5 and 6.

EXAMPLE 3

Amine-protein Stabilizers in the Control of Nematodes and Weeds

This example illustrates the efficacy of pre-plant applications of an aqueous formulation of $NaN_3$ for control of plant parasitic nematodes and weeds in a microplot experiment with tomato [*Lycopersicon esculentum*]. $NaN_3$ was stabilized in the formulation by means of a mixture of amines and the commercially available protein, casein. The formulation contained 5% [w/v] $NaN_3$ dissolved in demineralized water containing 2% [v/v] of a 10% [w/v] casein solution in ethanolamine. Soil in the microplots was a sandy loam [pH=6.2; organic matter content <1.0%; C.E.C <10 meq/100 g soil] infested with the nematodes: *Meloidogyne incognita, Paratrichodorus minor, Tylenchorhynchus claytoni,* and *Helicotylenchus dihystera* 1]. Weeds in the plots were principally crabgrass [*Digitaria sanguinalis*], yellow nutsedge [*Cyperus esculentum*], pigweed [*Amaranthus* spp.], and morning glories [*Ipomea* spp., *Jacquemontia tamnifolia*].

$NaN_3$ was applied to the 1-ft$^2$ microplots by drenching [2 L/plot] at amounts of: 0, 0.5, 1.0, 1.5, 2.0, 3.0, 4.0, and 5.0 g/plot. The plots were covered with standard polyethylene [1 mil] tarp immediately after application of the chemical. After 10 days the cover was removed, the number of weeds was determined, soil samples for nematological analyses were taken and each plot was planted with two 4-week old 'Huskie' tomato seedlings. The plants were grown for 3 months and data were collected on yield, number of fruits, weed infestation and nematode populations.

Soil samples from plots treated with $NaN_3$ did not contain nematodes, but the soil samples from the control plots had significant numbers of all nematode species. At planting time, there were no weeds in plots treated with all but the three lowest rates of $NaN_3$. Yield and number of fruits increased directly in response to $NaN_3$ rates from 0–4 g/plot. At the end of the experiment there were no plant parasitic nematodes in $NaN_3$-treated plots for all rates of application.

Figure 7:
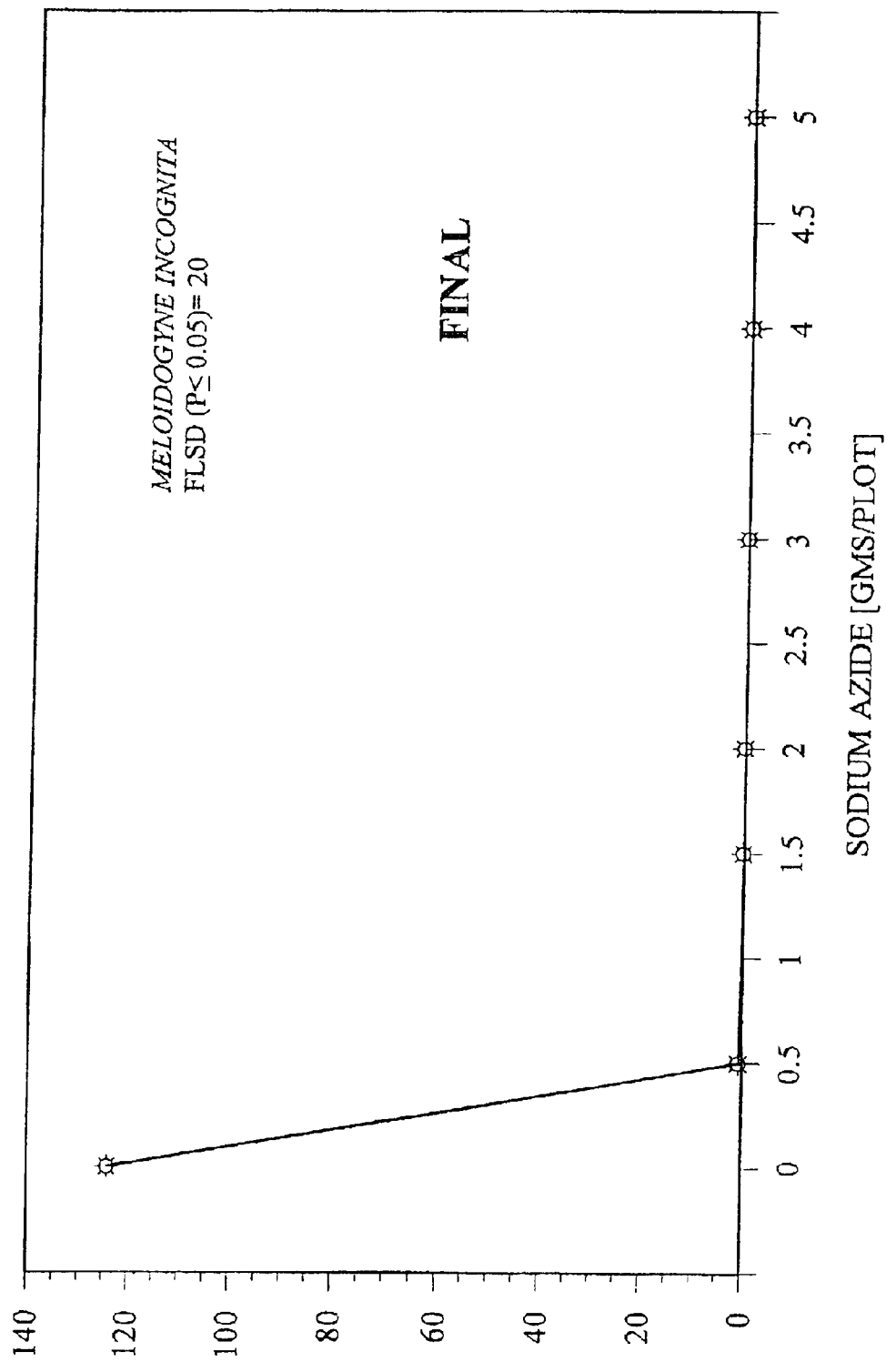
FIG. 7 depicts a graph illustrating the count of the nematode *Meloidogyne incognita* in soil treated with increasing doses of an aqueous solution of sodium azide in a mixture of amines and proteins.
Figure 8:
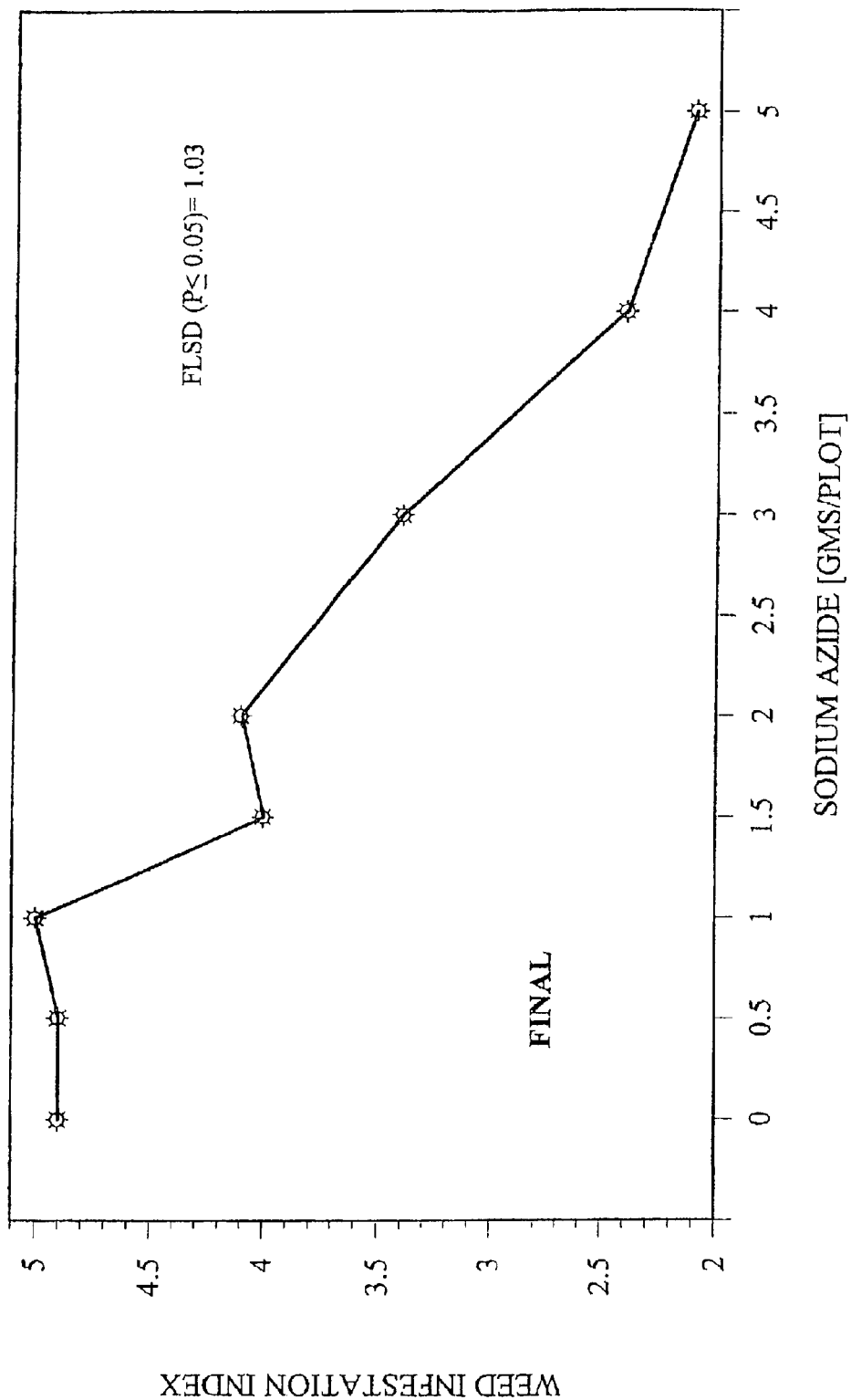
FIG. 8 is a graph illustrating the weed count or infestation in soil treated with increasing doses of an aqueous solution of sodium azide in a mixture of amines and proteins.
Figure 9:
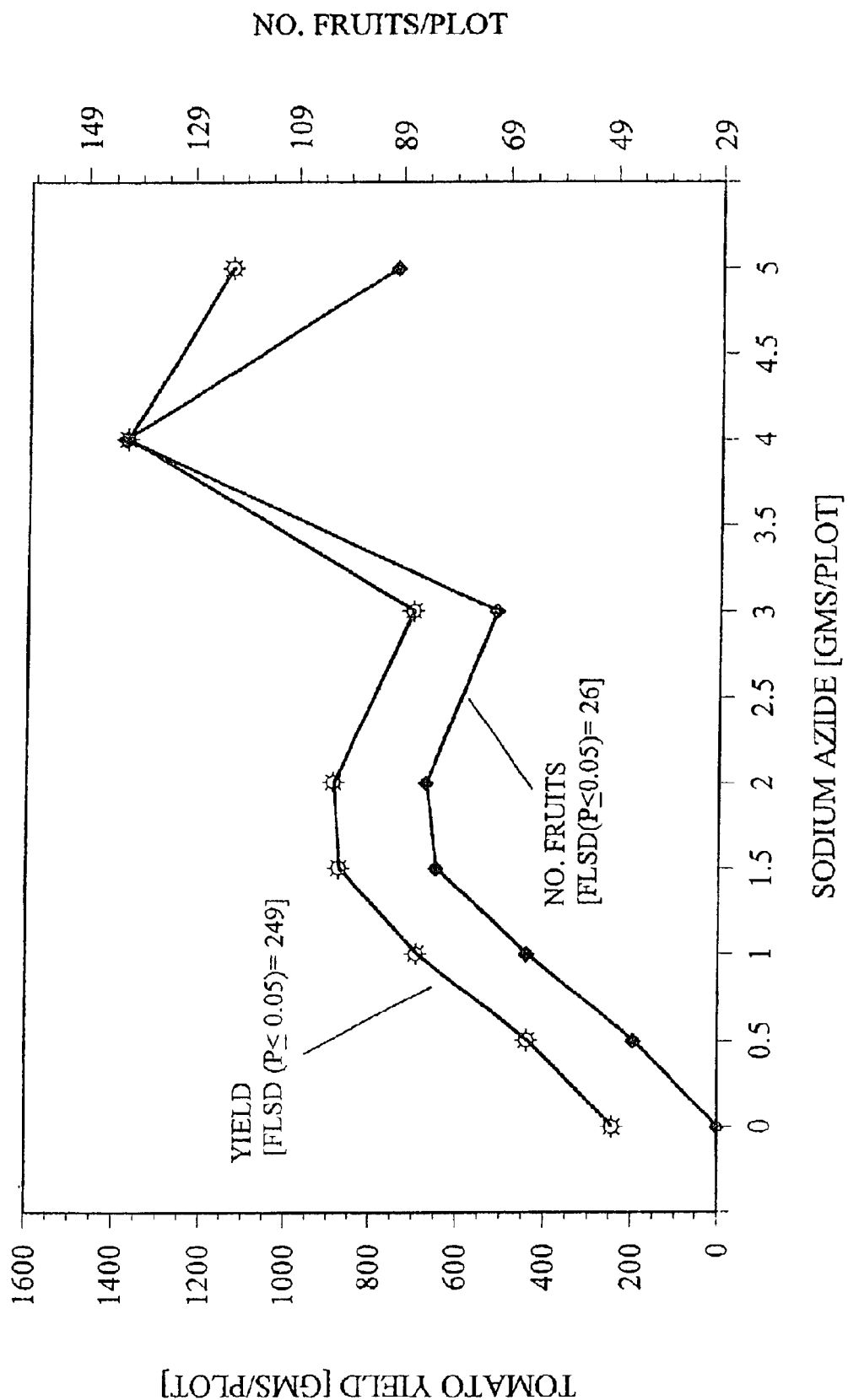
FIG. 9 depicts a graph comparing the number of fruits and yield of tomato plants grown in soil treated with increasing doses of an aqueous solution of sodium azide in a mixture of amines and proteins.

Final weed counts were inversely related to $NaN_3$ rate in a pattern described [$R^2=0.95^{**}$] by W=−0.32X+5.82, where W represents total weed population density/microplot and X, azide rates in gms $NaN_3$/plot. Results indicate that the amine-protein formulation is superior for nematode control and equal in herbicidal activity to formulations stabilized with inorganic buffers. The data also suggest that it is possible to deliver $NaN_3$ into soil together with organic compounds that can serve as plant nutrients and stimulate beneficial soil microbial activities. The results of Example 3 are illustrated in FIGS. 7–9.

EXAMPLE 4

Control of Root-knot Nematode and Weeds in Green Peppers and Tomatoes

This example illustrates the efficacy of pre-plant applications of $NaN_3$ for control of root-knot nematode [*Meloidogyne incognita*], coastal bermuda grass [*Cynodon dactylon*], yellow nutsedge [*Cyperus esculentum*] and other weeds in pepper [*Capsicum annum*] and tomato [*Lycopersicon esculentum*]. The soil was a calcareous silty clay loam with pH 7.8 and <1% organic matter. The $NaN_3$ was applied at drenching rates of 100 and 200 kg/ha using a solution of sodium azide in sodium lauryl sulfate. Each dosage rate was delivered into pre-acidified soil as well as in non-acidified and administered using 3 different water levels: 3, 10, and 15 L/m$^2$. Acidification was with $H_2SO_4$ to lower soil pH to less than 7.00. The soil was covered with standard polyethylene tarp immediately after $NaN_3$ application. After 3 weeks the soil was uncovered and a soil sample was removed for nematological analyses and the weeds were counted. Tomato and pepper seedlings were then transplanted 6 weeks after $NaN_3$ application.

Azide applications effectively controlled greater than 90% of the nematodes and all weeds at dosages of 100 and 200 kgs. The compound was particularly effective against nutsedge. $NaN_3$ performed well when drenched with any of the 3 water levels. There was no evidence of phytotoxicity to pepper or tomato plants in any of the plots treated with $NaN_3$.

EXAMPLE 5

Nematicidal and Herbicidal Properties of Potassium Azide

In this example, the nematotoxic properties of liquid potassium azide $KN_3$ are illustrated using soil from a cotton field infested with the reniform nematode (*Rotylenchulus reniformis*). The liquid potassium azide compound was added to the soil in an aqueous solution of amounts of: 1, 2, 3, 4 and 5 mgs $KN_3$ per kg of soil. The formulation used for this experiment 1% $KN_3$ and 0.5% sodium lauryl sulfate. Soil samples were collected one week after the application of the $KN_3$ solution for nematological analysis using such techniques as the salad bowl incubation technique. From the analysis it was shown that the numbers of reniform nematode declined exponentially in response to the increasing $KN_3$. Rates of 4–5 mg of $KN_3$ per kg of soil showed an almost 100% control of the reniform nematodes. Numbers of microbivorous nematodes declined in an almost linear fashion in response to the increasing dosages of $KN_3$.

In the application of $KN_3$ rates of 20–200 mg/kg of soil applied to a soil infested with crab grass (*Digitaria sanguinalis*), purple nutsedge (*Cyperus rotundus*), Jimson weed (*Datura stramonium*) and a variety of other weeds resulted in the number of weeds declining in proportion to rates used. Rates of greater than 140 mg/kg of soil resulted in over 80% control rates for weeds.

EXAMPLE 6

Azide-Casein Formulation Used to Control Deleterioius Organisms and to Stimulate Soil Microbial Activity In this example, the soil used was from a cotton field infested with the root-knot [*Meloidogyne incognita*], and lance [*Hoplolaimus galeatus*], nematodes—each a plant parasitic specie. The soil was mixed with washed siliceous river sand (in equal parts by volume), apportioned into one kg amounts in 4 L plastic bags and placed in pots. The test solution was prepared by dissolving 0.500 gms $KN_3$ in an aqueous solution containing 50 mls of a 10% casein [w/v] solution in 0.1N NaOH and diluting with water to a final volume of 500 mls; the solution thus contained 1 mg $KN_3$/ml. The solution was added to soil at rates of 1, 2, 4, 6, 8, and 10 mls/Kg soil. There were for each treatment and controls [no solution], a total of 7 pots each containing 1 Kg of soil. After application of the solution, for each rate, each pot was covered with a plastic bag. The pots were placed on a greenhouse bench and were arranged in a randomized block design. After 10 days the covers were removed, soil samples were collected from each pot for nematological analyses and "Young" soybean were planted [5 seed/pot]. The resulting plants were allowed to grow for 7 weeks when they were carefully separated from the soil and growth parameters measured. The roots and final soil samples were incubated to determine nematode populations. Nematode numbers in soil and roots were determined using the salad bowl incubation technique.

Figure 10:
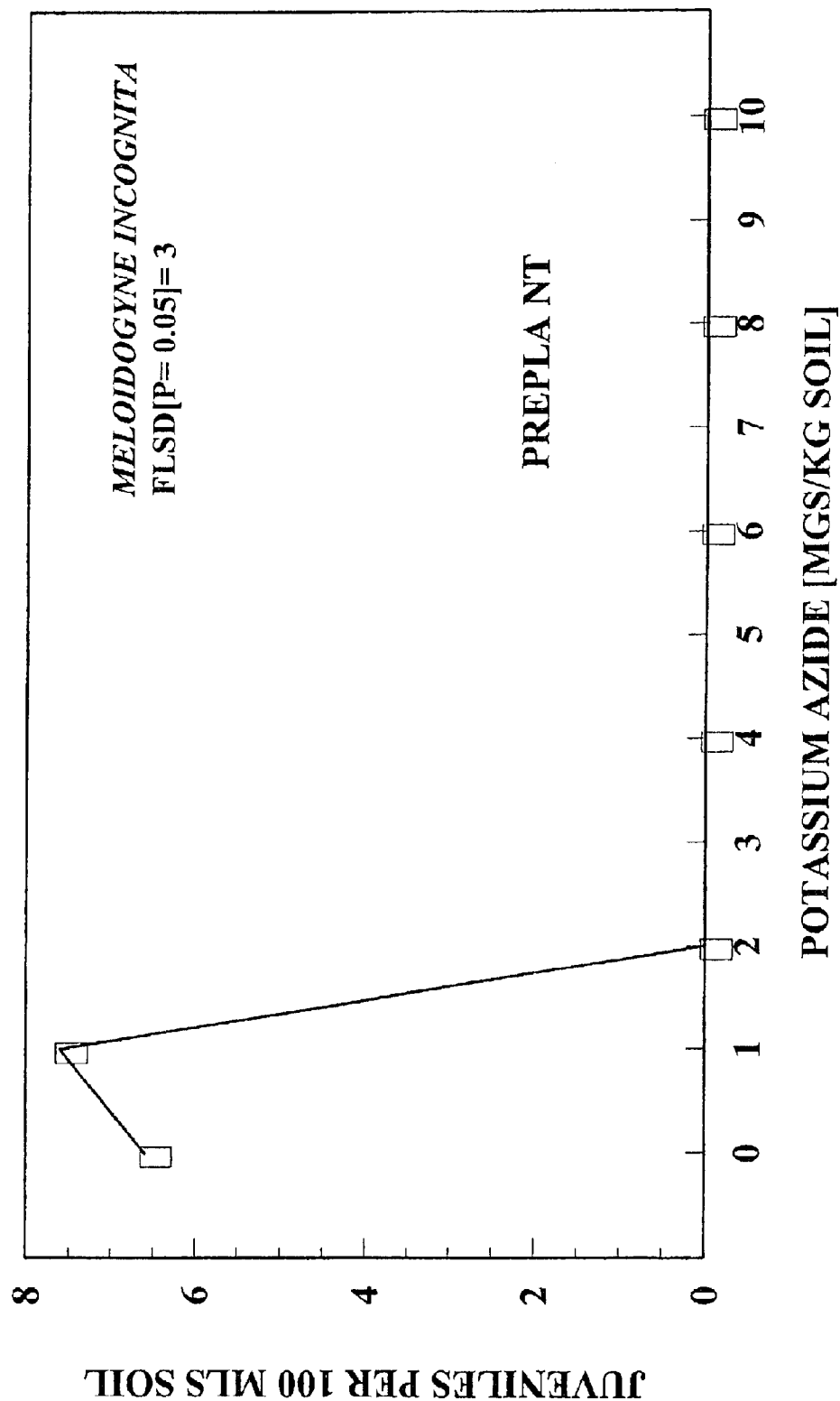
FIG. 10 is a graph illustrating the count of the deleterious nematode *meloidogyne incognita* in pre-plant soil treated with increasing doses of an aqueous solution of potassium azide and casein.
Figure 11:
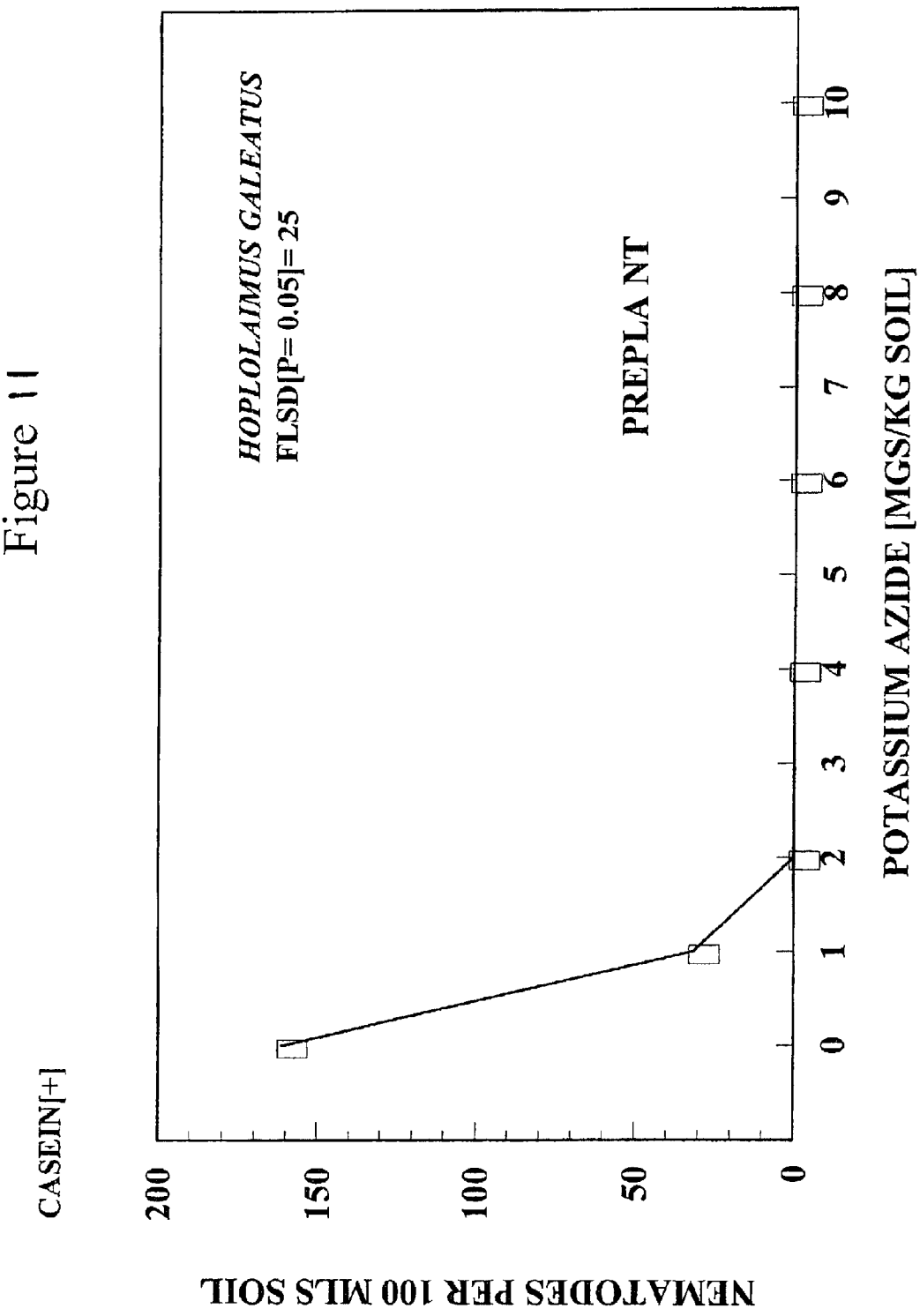
FIG. 11 is a graph illustrating the count of the deleterious nematode *hoplolaimus galeatus* in pre-planted soil treated with increasing doses of an aqueous solution of potassium azide and casein.
Figure 12:
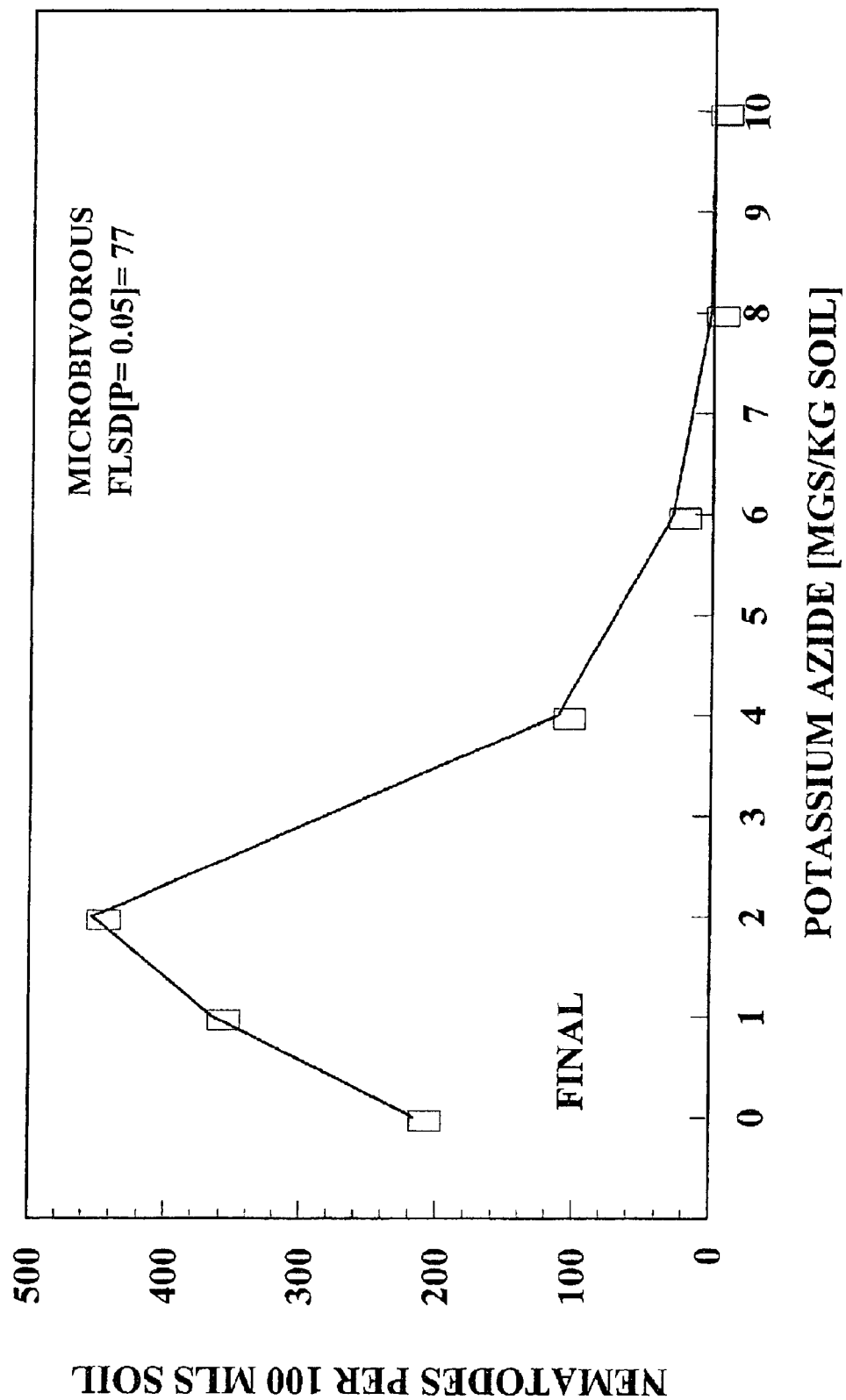
FIG. 12 is a graph illustrating the count of the beneficial microbivorous nematode in post-plant (final) soil treated with increasing doses of an aqueous solution of potassium azide and casein.

FIGS. 10 and 11 show that populations of the root-knot and lance nematodes in the preplant sample were eliminated by applications of $\geq 2$ mgs $KN_3$/Kg soil in these demonstrations. Significantly, as shown in FIG. 12 the populations of beneficial microbivorous nematodes were not adversely affected by application rates <6 $KN_3$/Kg. Indeed, the 1 and 2 mg application rates resulted in pronounced stimulation in the numbers of these beneficial nematodes. Applications of the azide at >4 mgs/Kg soils were necessary to significantly reduce or eliminate microbivorous nematodes, but these higher rates would not be required, since fully adequate control of deleterious organisms was achieved at the 2 mg level.

Figure 13:
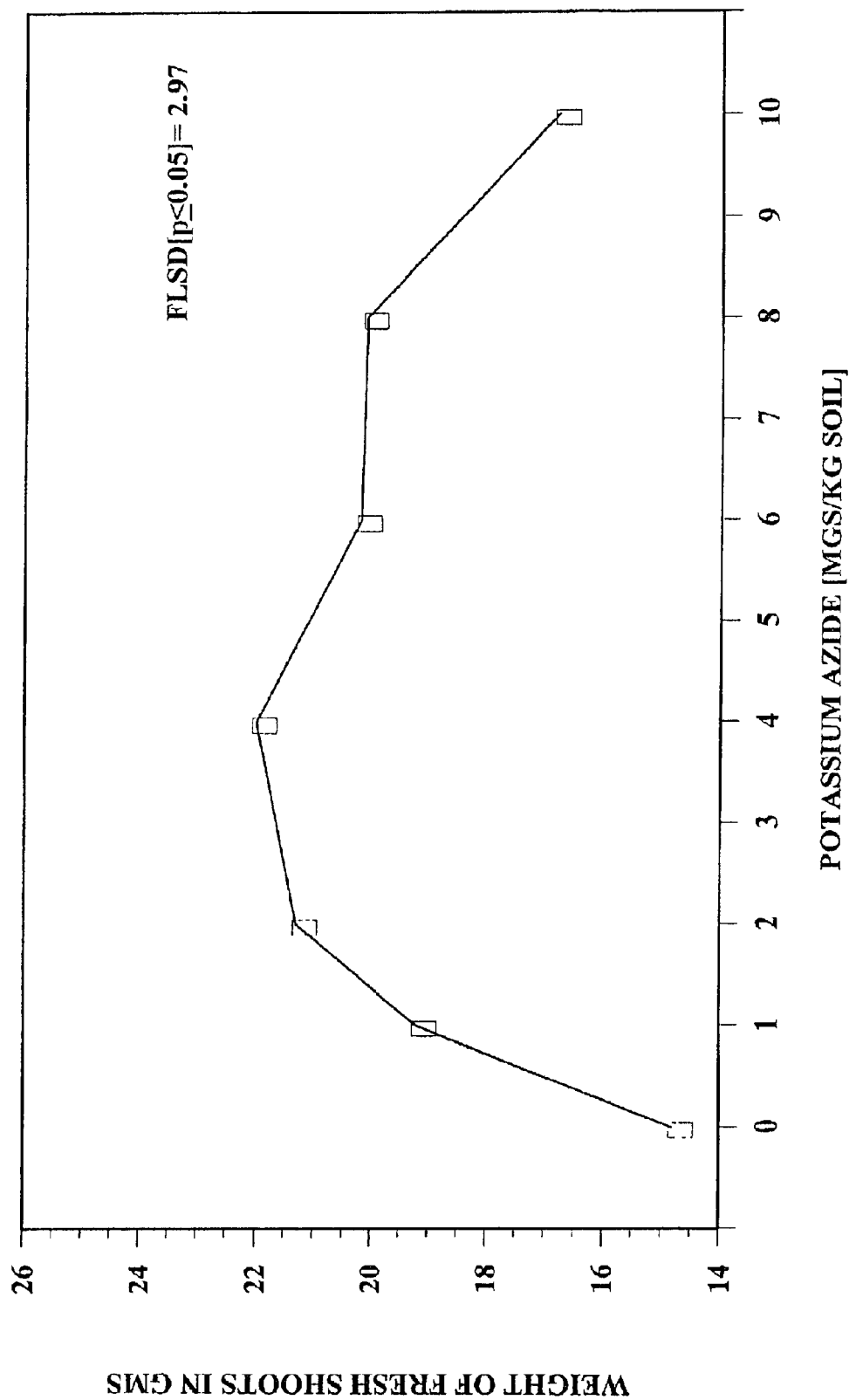
FIG. 13 is a graph illustrating the fresh shoot weight of soybean growth in soils treated with increasing doses of an aqueous solution of potassium azide and casein.
Figure 14:
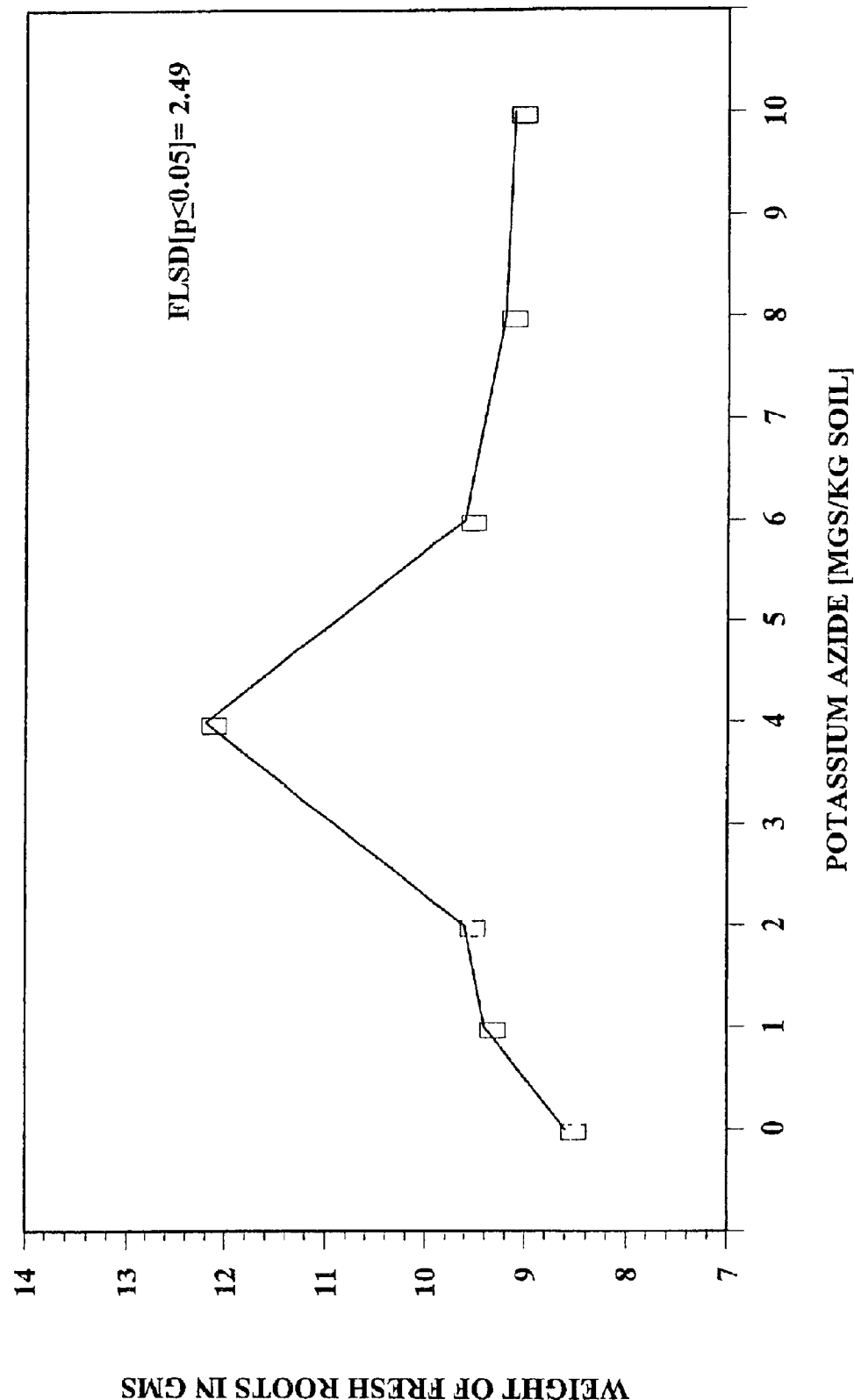
FIG. 14 is a graph illustrating the fresh root weight of soybean growth in soils treated with increasing doses of an aqueous solution of potassium azide and casein.

Plant response as measured by the weights of shoots and roots was positive and pronounced for pots in the range 1–8 mgs/Kg soil with particularly sharp increased values corresponding to the 1 and 2 mgs rates, as shown in FIGS. 13 and 14. This response coincided with increased microbivorous nematodes and the suppression or elimination of plant parasitic species. The data shows that $KN_3$ is a selective compound which at appropriate application rates, can eliminate plant parasitic nematodes while retaining or stimulating populations of beneficial microbivorous nematodes. The casein provided the substrate for development of a proteolytic microflora, principally bacteria that served as food for microbivorous nematodes, hence the observed increased numbers of these beneficial nematodes. The presence of microbivorous nematodes in soil is a good indicator of soil health in that they are an essential component for the decomposition and metabolism of organic matter in soil.

While specific embodiments have been set forth as illustrated and described above, it is recognized that variations may be made with respect to disclosed embodiments. Therefore, while the invention has been disclosed in various forms only, it will be obvious to those skilled in the art that many additions, deletions and modifications can be made without departing from the spirit and scope of this invention, and no undue limits should be imposed except as set forth in the following claims.

What is claimed is:

1. A composition for controlling a population of a deleterious soil organism comprising: a pesticidally effective amount of azide; and from about 5% to about 20% (w/v) of one or more polymers of amino acids of three more amino acids linked through peptide bonds, wherein said one or more polymers is not gelatin.

2. The composition of claim 1, further comprising a dispersal medium.

3. The composition of claim 2, wherein the dispersal medium is a liquid medium.

4. The composition of claim 3, wherein the liquid medium contains water.

5. The composition of claim 1, wherein the dispersal medium is a solid dispersal medium.

6. The composition of claim 1, wherein the azide is selected from the group consisting of a metal azide, an organic azide and combinations thereof.

7. The composition of claim 6, wherein the metal azide is an alkali metal azide selected from the group consisting of potassium azide, sodium azide, lithium azide, and combinations thereof.

8. The composition of claim 1, wherein the azide is ammonium azide.

9. The composition of claim 1, wherein the polymer is selected from the group consisting of oligopeptides, polypeptides, proteins and combinations thereof.

10. The composition of claim 9, further comprising a detergent selected from the group consisting of Tween 20 (polyoxyethylen (20) sorbitan monolaurate); Tween 40 (polyoxyethylene (20) sorbitan monopalmitate); Tween 60 (polyoxyathylene (20) sorbitan monostearate); Tween 80 (polyox ethylene (20) sorbitan monostearatepalmitate); Tween 85 (polyoxyethylene (20) sorbitan trioleate); tergitol; sodium lauryl sulfate, and combinations thereof.

11. The composition of claim 9, further comprising an amine selected from the group consisting of primary, secondary and tertiary aryl or alkylamines and mixtures thereof.

12. The composition of claim 9, further comprising pH buffering agent selected from the group consisting of ethanolamine, dimethylamine, ethylamine, butylamine, diethylamine, diethanolamine, monoethanolamine, diethylethanolamine and phenylethylamine, and combinations thereof.

13. The composition of claim 9, wherein the polypeptide is a protein selected from the group consisting of proteins derived from a cereal meal, zein, gluten, casein, proteins obtained from whey and mixtures thereof.

14. The composition of claim 13 wherein the protein is casein.

15. The composition of claim 2 wherein the azide comprises up to about 40% based upon the weight of the dispersal medium.

16. The composition of claim 15 wherein the dispersal medium is a liquid medium, and the azide comprises up to about 20% and the polymer up to about 10%, each based upon the weight of the liquid medium.

17. A composition for controlling a population of a deleterious soil organism and stimulating the activities of proteolytic microorganisms comprising: aqueous liquid medium; a pesticidally effective amount of azide salt selected from the group consisting of sodium azide and potassium azide; and from about 5% to about 20% (w/v) of one or more polymers of three or more amino acids linked through peptide bonds, wherein said one or more polymers is not gelatin.

18. The composition of claim 17, wherein the polymer is selected from the group consisting of oligopeptides, polypeptides, proteins and combinations thereof.

19. A method of controlling a population of a deleterious soil organism, in soil, comprising the step of: applying to a soil composition comprising azide, a liquid medium, and polymer of amino acids of three or ore amino acids linked through peptide bonds, wherein said polymer is not gelatin, the amount of azide in the soil is effective for controlling a population of a deleterious organism therein, and the amount of the polymer is effective for stimulating the activities of proteolytic microorganisms.

20. The method of claim 19, wherein the amount of azide in the soil effective for controlling the population of a deleterious organism therein is in the range of about 1 to about 200 mg per kg of soil.

21. The method of claim 19, wherein the composition is applied, prior to planting, to the areas of the soil in which the plant's roots will grow.

22. The method of claim 17, in which the composition further comprises an additive selected from the group consisting of detergents, pH buffering agents, alkalis, amines and combinations thereof.

23. The method of claim 22, wherein the detergent is selected from the group consisting of Tween 20 (poiyoxyethylene (20) sorbitan monolaurate); Tween 40 (polyoxyethylene (20) sorbitan monopalmitate); Tween 60 (polyoxyethylene (20) sorbitan monostearate); Tween 80 (polyoxyethylene 20) sorbitan monostearatepalmitate); Tween 85 (polyoxyethylene (20) sorbitan trioleate ; tergitol; sodium lauryl sulfate, and combinations thereof.

24. The method of claim 22, wherein the pH buffering agent is selected from the group consisting essentially of Tris buffer, ammonium phosphate, sodium phosphate, potassium phosphate, ammonium carbonate, sodium carbonate, potassium carbonate, ammonium citrate, sodium citrate, potassium citrate, and combinations thereof.

25. The method of claim 22, wherein amine is selected from the group consisting of primary, secondary and tertiary aryl or alkyl amines and combinations thereof.

26. The method of claim 19, wherein the polymer is a protein selected from the group consisting of proteins derived from cereal meal, zein, gluten, casein, proteins obtained from whey, and mixtures thereof.

27. The method of claim 19, wherein the azide is selected from the group consisting of a metal azide, an organic azide and combinations thereof.

28. The method of claim 27, metal azide is an alkali metal azide selected from the group consisting of potassium azide, sodium azide, lithium azide, and combinations thereof.

29. The method of claim 19 wherein the composition comprises up to about 40% of azide and up to about 20% of the polymer, each based upon the weight of the liquid medium.

30. The method of claim 19 wherein the azide is sodium azide and the polymer is casein.

31. The method of claim 30 wherein the sodium azide comprises up to 20% and the casein comprises up to 10%, each based upon the weight of the liquid medium.

32. A method for delivering a pesticidal composition comprising: applying to soil a pesticidal composition prior to planting, to the areas of the soil in which the plant's roots are to grow, wherein the pesticidal composition comprises an aqueous liquid medium, azide selected from the group consisting of potassium azide and sodium azide, and amino acid polymer selected from the group consisting of oligopeptides, polypeptides and proteins, with the proviso that said polymer is not a gelatin.

33. The method of claim 32 wherein the applying is by drip irrigation.

34. A kit for preparing a pesticidal composition comprising packaging and having therein an azide, a polymer of amino acids of three or more amino acids linked through peptide bonds and instructions for preparing a pesticidal composition and applying the pesticidal composition to a soil, thereby reducing a population of deleterious organisms therein and stimulating the activities of proteolytic microorganisms, wherein the pesticidal composition comprises pesticidally effective amount of azide and from about 5% to about 20% (w/v) of one or ore polymers of amino acids of three or more amino acids linked through peptide bonds, wherein said one or more polymers is not gelatin.

35. The kit of claim 34 further comprising a dispersal medium, wherein the dispersal medium is a liquid medium.

* * * * *

UNITED STATES PATENT AND TRADEMARK OFFICE
CERTIFICATE OF CORRECTION

PATENT NO. : 6,852,341 B2
DATED : February 8, 2005
INVENTOR(S) : Rodrigo Rodriguez-Kabana It is certified that error appears in the above-identified patent and that said Letters Patent is hereby corrected as shown below:

Column 12,
Line 22, after "three" insert -- or --.
Line 47, delete "polyoxyethylen" and insert -- polyoxyethylene --.
Line 49, delete "polyoxyathylene" and insert -- polyoxyethylene --.
Line 50, delete "polyox ethylene" and insert -- polyoxyethylene --.

Column 13,
Line 10, after "comprising" insert -- an --.
Line 22, after "soil" insert -- a --.
Line 23, delete "ore" and insert -- more --.
Line 42, delete "poiyoxyethytene" and insert -- polyoxyethylene --.
Line 45, delete "20)" and insert -- (20) --.
Line 46, after "trioleate" insert -- ) --.

Column 14,
Lines 43-44, after "comprises" insert -- a --.
Line 45, delete "ore" and insert -- more --.

Signed and Sealed this

Twenty-fifth Day of April, 2006

JON W. DUDAS
*Director of the United States Patent and Trademark Office*